(12) United States Patent
Stopek et al.

(10) Patent No.: US 8,309,222 B2
(45) Date of Patent: Nov. 13, 2012

(54) COATED FILAMENTS

(75) Inventors: Joshua Stopek, Yalesville, CT (US); Brian Cuevas, Cumming, GA (US); Joseph Hotter, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 11/789,531

(22) Filed: Apr. 25, 2007

(65) Prior Publication Data
US 2008/0268243 A1    Oct. 30, 2008

(51) Int. Cl.
| | |
|---|---|
| D02G 3/36 | (2006.01) |
| A61B 17/04 | (2006.01) |
| B05D 7/24 | (2006.01) |
| C08L 67/04 | (2006.01) |
| C08L 77/02 | (2006.01) |

(52) U.S. Cl. ....... 428/378; 606/231; 427/2.31; 525/415; 525/419

(58) Field of Classification Search .................. 424/422; 623/1.11; 427/2.31; 606/230–234
See application file for complete search history.

(56) References Cited

U.S. PATENT DOCUMENTS

| | | | |
|---|---|---|---|
| 3,987,797 A | 10/1976 | Stephenson | |
| 4,027,676 A | 6/1977 | Mattei | |
| 4,624,256 A | 11/1986 | Messier et al. | |
| 4,983,180 A * | 1/1991 | Kawai et al. ................. | 606/230 |
| 5,089,013 A | 2/1992 | Bezwada et al. | |
| 5,123,912 A | 6/1992 | Kaplan et al. | |
| 5,147,383 A | 9/1992 | Bezwada et al. | |
| 5,352,515 A | 10/1994 | Jarrett et al. | |
| 5,530,074 A | 6/1996 | Jarrett et al. | |
| 5,688,855 A * | 11/1997 | Stoy et al. ...................... | 524/505 |
| 5,814,068 A | 9/1998 | Koike et al. | |
| 5,925,065 A * | 7/1999 | Totakura et al. ............... | 606/229 |
| 6,143,037 A | 11/2000 | Goldstein et al. | |
| 6,451,339 B2 * | 9/2002 | Patel et al. ..................... | 424/451 |
| 6,653,423 B1 | 11/2003 | Yamamoto et al. | |
| 6,706,260 B1 | 3/2004 | Tanaka et al. | |
| 6,723,350 B2 | 4/2004 | Burrell et al. | |
| 6,765,069 B2 | 7/2004 | Zamora et al. | |
| 2002/0106780 A1 * | 8/2002 | Fiscella et al. ................ | 435/226 |
| 2003/0069369 A1 * | 4/2003 | Belenkaya et al. ............ | 525/437 |
| 2003/0091641 A1 | 5/2003 | Tiller et al. | |
| 2003/0091827 A1 | 5/2003 | Zamora et al. | |
| 2003/0203991 A1 | 10/2003 | Schottman et al. | |
| 2004/0037871 A1 | 2/2004 | Healy et al. | |
| 2004/0147629 A1 * | 7/2004 | Roby ............................. | 523/105 |
| 2004/0157073 A1 | 8/2004 | Burrell et al. | |
| 2004/0258931 A1 | 12/2004 | Zamora et al. | |
| 2005/0175667 A1 | 8/2005 | Carlyle | |
| 2006/0003008 A1 * | 1/2006 | Gibson et al. ................. | 424/486 |
| 2006/0193884 A1 | 8/2006 | Stopek et al. | |

FOREIGN PATENT DOCUMENTS

GB     2 064 556 A     6/1981
(Continued)

OTHER PUBLICATIONS

Wasan et al. "Role of Plasma Lipoproteins in Modifying Biological Activity of Hydrophobic Drugs". Journal of Pharmaceutical Sciences, vol. 87, No. 4. (1998), pp. 411-424.*

(Continued)

*Primary Examiner* — Maria Veronica Ewald
*Assistant Examiner* — Prashant J Khatri

(57) ABSTRACT

The present disclosure describes a coating for a surgical filament including a vinyl lactam polymer and a lactone polymer.

21 Claims, 1 Drawing Sheet

FOREIGN PATENT DOCUMENTS

US      EP0558965 A2 *  9/1993

OTHER PUBLICATIONS

Lele et al. "Synthesis and Micellar Characterization of Novel Amphiphilic A-B-A Triblock Copolymers of N-(2-Hydroxypropyl) methacrylamide or N-Vinyl-2-pyrrolidone with Poly(epsilon-caprolactone)". Macromolecules, vol. 35, No. 17. (2002), pp. 6714-6723.*

Tan et al. "Fabrication of double-walled microspheres for the sustained release of doxorubicin". Journal of Colloid and Interface Science, vol. 291, (2005), pp. 135-143.*

Vascufil™ website. http://www.covidien.com/syneture/pageBuilder.aspx?webPageID=0&topicID=329&xsl=xsl/productPagePrint.xsl. (2008).*

Materials Safety Data Sheet: Poloxamer 188, Surfactant MSDS (2005).*

Escobar-Chavez et al. "Applications of Thermoreversible Pluronic F-127 Gels in Pharmaceutical Formulations". J Pharm Pharmaceut Sci, 9 (3), 339-358. Published Nov. 27, 2006.*

International Search Report from Application PCT/US07/26003 dated Apr. 16, 2008.

European Search Report for EP 08251495.1-2108 date of completion is Sep. 30, 2008 (8 pages).

* cited by examiner

COATED FILAMENTS

BACKGROUND

1. Technical Field

The present disclosure relates to filaments, and more particularly to coated surgical filaments.

2. Background of Related Art

Surgical filaments may be coated to enhance certain physical characteristics of the filament, such as tensile strength and the ease of a sliding a knot into place on the filament, commonly referred to as knot repositioning or knot run down. Filament coatings have included lubricants, oils, adhesives, antibacterial agents and a wide variety of polymeric materials. Although previously discovered filament coatings have been sufficient for performing their intended use, room for improvement remains for filament coatings in the areas of drug delivery.

SUMMARY

The present disclosure describes coated filaments. One or more of the filaments may be utilized to form a variety of surgical devices, e.g., sutures, meshes, etc. The filaments are coated with a vinyl lactam containing composition. In embodiments, the composition is containing a blend of a vinyl lactam polymer and a lactone polymer. In embodiments, the coating forms a smooth, single phase surface. In other embodiments, the coating forms a partitioned multiphase surface on the filaments. In embodiments, the filaments are pre-coated with a base coating prior to application of the composition containing a vinyl lactam polymer.

Additionally, filaments are described including a multiphase coating containing a blend of hydrophilic polymers and hydrophobic polymers. In embodiments, the polymers may be combined with hydrophilic or hydrophobic drugs. Methods of controlling phase separation of a coating are also disclosed.

DETAILED DESCRIPTION OF PREFERRED EMBODIMENTS

Figure 1:
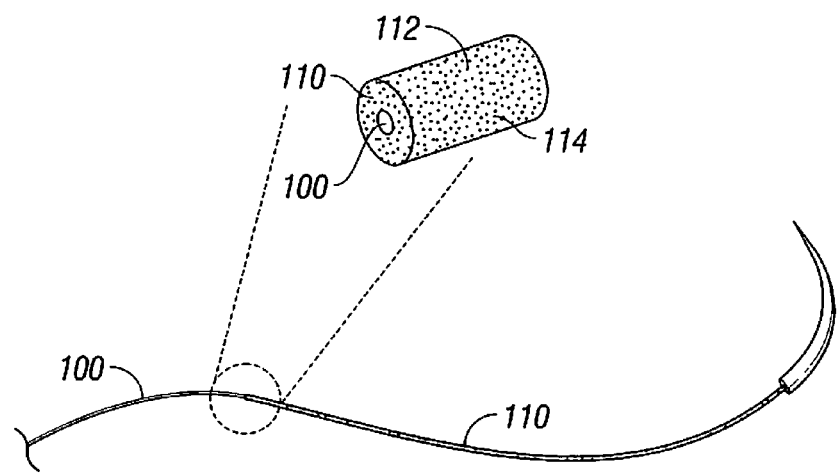
FIG. 1 shows a perspective view of a coated filament in accordance with a multi-phase embodiment described herein.

The present disclosure relates to surgical filaments having a coating containing a vinyl lactam polymer. The coated filaments described herein may be used to form a variety of medical devices which include, but are not limited to, sutures, staples, meshes, patches, slings, stents, drug delivery devices, wound dressings, woven devices, non-woven devices, braided devices, knitted devices, adhesion barriers, and other implantable devices. The filaments may form monofilament or multifilament devices.

The filaments can be formed from any sterilizable biocompatible material that has suitable physical properties for the intended use of the filament. The filaments can be made from synthetic or natural polymers that are either bioabsorbable or non-bioabsorbable. Some specific non-limiting examples of suitable absorbable materials include trimethylene carbonate, caprolactone, dioxanone, glycolic acid, lactic acid, glycolide, lactide, homopolymers thereof, copolymers thereof, and combinations thereof. Some specific non-limiting examples of suitable non-absorbable materials which may be utilized to form the filaments include polyolefins, such as polyethylene, polypropylene, copolymers of polyethylene and polypropylene, and blends of polyethylene and polypropylene. It should, of course, be understood that combinations of materials may be used to form the filaments.

Methods for preparing compositions suitable for making filaments as well as techniques for making filaments from such compositions are within the purview of those skilled in the art.

The filaments described herein include a coating that contains a vinyl lactam polymer. Any vinyl lactam polymer may be included in the composition used to form the coating. As used herein, the term "vinyl lactam polymer" means any polymer that may be derived from, synthesized from, or prepared with at least one lactam monomer of the following formulas:

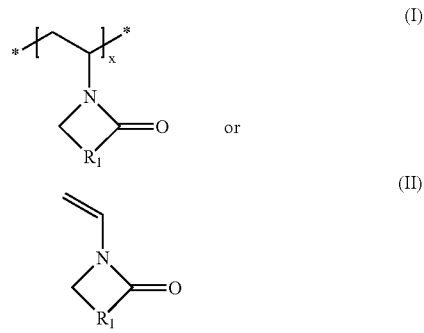

wherein $R_1$ represents a $C_1$-$C_4$ alkyl, alkenyl, or alkadienyl bridge group necessary to complete a 4, 5, 6 or 7-membered heterocyclic ring system; and x represents an integer from 0 to 50.

In embodiments, the vinyl lactam polymer includes at least one of the following monomeric units: N-vinyl-2-pyrrolidone, N-vinyl-2-piperidone, and N-vinyl-caprolactam, N-vinyl methyl pyrrolidone, N-vinyl ethyl pyrrolidone, N-vinyl methyl caprolactam, vinyl pyrrolidone, vinyl caprolactam, vinyl piperidone and combinations thereof. The vinyl lactam polymer may be a homopolymer or a copolymer, such as a random copolymer, a block copolymer, graft copolymer or a segmented copolymer. Any monomer which can be copolymerized with a vinyl lactam monomer to provide a biocompatible polymer may be used to form the copolymer. Suitable comonomers includes, but are not limited to, hydrophilic vinyl monomers, such as methacrylic acid, acrylic acid, acrylamide, sodium acrylate, sulfopropyl acrylate, sulfopropyl methacrylate, vinyl functionalized phosphorylcholine, hydroxyl ethyl methacrylate, methacrylamide, niipam and the like.

Generally, the vinyl lactam polymer may represent from about 0.01% to about 100% by weight of the composition coating. In embodiments, the vinyl lactam polymer represents from about 0.1% to about 25% by weight of the coating.

In embodiments, the coating composition includes a lactone polymer in addition to the vinyl lactam polymer. Any known lactone polymer may be used in forming the filament coating. As used herein, the term "lactone polymer" means any polymer that may be derived from, synthesized from, or prepared with at least one lactone monomer of the following formula:

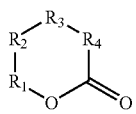

wherein the $R_1$, $R_2$, $R_3$ and $R_4$ groups may independently represent one of the following, an oxygen atom, a carbonyl group, or a linear, branched or cyclic $C_1$ to $C_{20}$ alkyl, alkenyl, alkadienyl group.

The lactone polymer may be a homopolymer or a copolymer, such as a random copolymer, a block copolymer, graft copolymer, or a segmented copolymer. Any monomer which can be copolymerized with a lactone monomer to provide a biocompatible polymer may be used to form the copolymer. Suitable comonomers includes, but are not limited to alkylene oxides, acrylates, acrylamides and saccharides (e.g., dextrin). In embodiments the lactone polymer includes at least one of the following monomeric units: lactide, glycolide, caprolactone, dioxanone, propiolactone, butyrolactone, valerolactone, decalactone, pivalolactone, stearolactone, palmitolactone, trimethylene carbonate and combinations thereof. In particularly useful embodiments, the lactone polymer contains caprolacatone, glycolide, lactide and combinations thereof.

Generally, the lactone polymer may represent up to about 99% by weight of the coating. In embodiments, the lactone polymer represents from about 5% to about 95% by weight of the coating.

In embodiments, the vinyl lactam polymer and the lactone polymer may be combined in a solvent which both polymers are mutually soluble to form the coating composition. Examples of suitable solvents include but are not limited to chlorinated solvents, chloroform, methylene chloride, 1,1,2-trichloroethane, trifluoroethanol, methyl acetate, ethyl acetate, amyl acetate, acetone, tetrahydrofuran, 1,3-dioxolane, 1,4-dioxane, cyclohexanone, ethyl formate, 2,2,2-trifluoroethanol, 2,2,3,3-tetrafluoro-1-propanol, 1,3-difluoro-2-propanol, 1,1,1,3,3,3-hexafluoro-2-methyl-2-propanol, 1,1,1,3,3,3-hexafluoro-2-propanol, 2,2,3,3,3-pentafluoro-1-propanol, and nitroethane.

The coatings described herein may be applied to a filament by any technique, including but not limited to coating, dipping, spraying, brushing or any other appropriate techniques for forming a continuous layer onto the surface of an implantable device. The particular technique used may be chosen by those skilled in the art based on a variety of factors such as the specific construction of the surgical filament and the material contained in the coating.

The filament coating may be applied to the surgical filament as single layer or as a multilayer configuration. Each layer of the multilayer configuration may contain a different composition, provided that at least one layer is formed from a vinyl lactam polymer containing composition. The individual layers may also be arranged in any order or configuration including alternating layers, sandwich like structures, multiple monolayers and combinations thereof.

In embodiments, the filament may be pre-coated with a base coating prior to application of a composition containing a vinyl lactam polymer. The base coating material may include any biocompatible, natural or synthetic, bioabsorbable or nonbioabsorbable material capable of being applied to a surgical filament. Some examples of useful base coating materials include, but are not limited too, silicone, beeswax, polytetrafluoroethylene, nylons, fibrin, collagen, fibrinogen, albobumin, acrylates, such as polyacrylates, methacrylates, sulfopropyl acrylates, potassium sulfopropyl acrylates, sodium acrylates, and hydroxyethoxymethylacrylate; lactones and cyclic lactones; polyamides; polyamines, such as poly(styrene sulfonic acid), poly(acrylic acid), poly(methacrylic acid), poly(vinyl sulfonic acid), poly(vinyl sulfuric acid), poly(vinyl boric acid), poly(styrene boric acid), poly (vinyl phosphoric acid), and poly(styrene phosphoric acid); polyalcohols, ethane diol, 1,3-propanediol, 1,2-propanediol, 2-methyl-1,3-propanediol, 1,4-butanediol, 1,3-butanediol, 1,6-hexanediol, neopentylglycol, glycerol, pentaerythritol, trimethylol propane, ditrimethylol propane, 1,4-cyclohexane dimethanol, the monoester of neopentylglycol and hydroxy pivalic acid, 2,2,4-trimethyl pentanediol, and dimethylol propionic acid, polyesterpolyols, and polyetherpolyols; phospholipids; phenylated vinyls compounds; vinyl acetates; lactone alkoxides; polybutylene terephthalate; polyalkylene oxides; polyalkylene glycols such as polyethylene glycol and polypropylene glycol; metallic salts such as calcium stearate, magnesium stearate; polyhydroxybutyrates; polyhydroxyalkoanates; and combinations thereof.

A second coating containing a vinyl lactam polymer may then be applied to the pre-coated filaments. In embodiments, the vinyl lactam polymer forms a separate layer on the pre-coated filaments. In addition, the second coating containing the vinyl lactam polymer may optionally further include a lactone polymer as described hereinabove.

In accordance with the certain embodiments of present disclosure, the coatings described herein may advantageously phase separate to form a partitioned filament coating. The partitioned coating allows for the polymers of the coating to be positioned along different portions of the filament. The separation of the polymers can be useful in delivering drugs to different portions of the filament. In embodiments such as these, the filament coating contains a blend of a hydrophilic polymer and a hydrophobic polymer. The hydrophilic polymers can be copolymers, homopolymers, random copolymers or block copolymers formed from the group consisting of: polyvinyl alcohol, vinyl lactams, polyvinylpyrrolidone, polyoxyethylene, polyacrylamide, poly(2-hydroxy-ethyl-methacrylate), polymethacrylamide, dextran, alginic acid, sodium alginate, polysaccharides, gelatine and copolymers The hydrophobic polymers can be copolymers, homopolymers, random copolymers, or block copolymers formed from the group consisting of: ε-caprolactone, glycolide, 1-lactide, d,l-lactide, d-lactide, meso-lactide, trimethylene carbonate, 4,4-dimethyl-1,3-dioxan-2-one, p-dioxanone, dioxepanone, Δ-valerolactone, β-butyrolactone, ε-decalactone, 2,5-diketomorpholine, pivalolactone, α,α-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, and other substituted glycolides, and substituted lactides. In particularly useful embodiments, the coatings include a blend of polyvinylpyrrolidone and a lactone polymer.

The partitioned coatings allow for drug delivery from either phase. For example, the hydrophilic polymers may be useful in delivering hydrophilic drugs to a certain portion of the coated filament. The term "drug" is meant to include any agent capable of rendering a therapeutic affect, such as, antimicrobial agents, anesthetics, angiogenic agents, fibrotic agents, antimitotics, chelating agents, peptides, proteins, DNA, RNA, nucleotides, liposomes, analgesics, blood products, hormones, water-soluble silver salts, growth factors and the like. Some specific non-limiting examples of hydrophilic drugs that may be used in the present filament coatings include, sirolimus, Taxol® (paclitaxel), chlorhexidine, polyhexamethylene, lidocaine, bupivicaine, thiamylal sodium, thiopental sodium, ketamine hydrochloride, flurazepam hydrochloride, amobarbital sodium, phenobarbital, bromovalerylurea, chloral hydrate, phenytoin sodium, ethotoin, phenobarbital sodium, trimethadione, primidone, ethosuximide, carbamazepine, sodium valproate, acetaminophen, phenacetin, aspirin, sodium salicylate, aminopyrine, antipyrine, sulpyrine, mepirizole, tiaramide hydrochloride, perixazole citrate, diclofenac sodium, anfenac sodium, buprenorphine hydrochloride, butorphanol tartrate, eptazocine hydrobromide, dimenhydrinate, difenidol hydrochloride, dl-isoprenaline hydrochloride, chlorpromazine hydrochloride, levomepromazine maleate, thioridazine hydrochloride, fluphenazine hydrochloride, thiothixene, flupenthixol hydrochloride, utyrophenone drugs: floropipamide hydrochloride, moperone hydrochloride, carpipramine hydrochloride, clocapramine hydrochloride, imipramine hydrochloride, desipramine hydrochloride, fluphenazine hydrochloride, thiothixene, flupenthixol hydrochloride, utyrophenone drugs: floropipamide hydrochloride, moperone hydrochloride, carpipramine hydrochloride, clocapramine hydrochloride, imipramine hydrochloride, desipramine hydrochloride, maprotiline hydrochloride, chlordiazepoxide hydrochloride, dipotassium clorazepate, meprobamate, hydroxyzine hydrochloride, saflazine hydrochloride, tetracaine hydrochloride, procaine hydrochloride, ethyl aminobenzoate, dibucaine hydrochloride, lidocaine hydrochloride, chlorphenesin carbamate, methocarbamol, acetylcholine chloride, neostigmine bromide, atropine sulfate, scopolamine hydrobromide, papaverine hydrochloride, biperiden hydrochloride, trihexyphenidyl hydrochloride, amantadine hydrochloride, piroheptine hydrochloride, profenamine hydrochloride, levodopa, mazaticol hydrochloride, diphenhydramine hydrochloride, carbinoxamine maleate, dl-chlorpheniramine maleate, clemastine fumarate, aminophylline, choline theophylline, caffeine and sodium benzoate, dl-isoproterenol hydrochloride, dopamine hydrochloride, dobutamine hydrochloride, propranolol hydrochloride, alprenolol hydrochloride, bupranolol hydrochloride, timolol maleate, metoprolol tartrate, procainamide hydrochloride, lidocaine hydrochloride, quinidine sulfate, ajmaline, verapamil hydrochloride, aprindine hydrochloride, hydrochlorothiazide, acetazolamide, isosorbide, ethacrynic acid, captopril, enalapril maleate, delapril hydrochloride, alacepril, hydralazine hydrochloride, hexamethonium bromide, clonidine hydrochloride, bunitrolol hydrochloride, propranolol hydrochloride, methyldopa, guanethidine sulfate, bethanidine sulfate, phenylephrine hydrochloride, methoxamine hydrochloride, diltiazem hydrochloride, varapamil hydrochloride, isosorbide dinitrate, nicorandil, nicametate citrate, nicotinic-alcohol tartrate, tolazoline hydrochloride, nicardipine hydrochloride, ifenprodil tartrate, piperidinocarbamate, cinepazide maleate, thiapride hydrochloride, dimorpholamine, levallorphan tartrate, naloxone hydrochloride, hydrocortisone, dexamethasone sodium phoshpate, prednisolone, norethisterone, clomiphene citrate, tetracycline hydrochloride, methyl salicylate, isothipendyl hydrochloride, diphenhydramine, prednisolone, ethyl aminobenzoate, crotamiton, salicylic acid, nystatin, econazole nitrate, cloconazole hydrochloride, vitamin $B_1$, cycothiamine hydrochloride, vitamin $B_2$ vitamin $B_6$, nicotinic acid, nicotinamide, calcium pantothenate, pantothenol, panthetin, biotin, ascorbic acid, tranexamic acid, ethamsylate, protamine sulfate, colchicine, allopurinol, tolazamide, glymidine sodium, glybuzole, metformin hydrochloride, buformin hydrochloride, orotic acid, azathioprine, lactulose, nitrogen mustard N-oxide hydrochloride, cyclophophamide, thio-TEPA, nimustine hydrochloride, thioinosine, fluorouracil, tegafur, vinblastine sulfate, vincristine sulfate, vindesine sulfate, mitomycin C, daunorubicin hydrochloride, aclarubicin hydrochloride, procarbazine hydrochloride, cisplatin, benzylpenicillin potassium, amoxicillin, penicillin, oxycillin, methicillin, carbenicillin, ampicillin, cefalexin, cefazolin, erythromycin, kitasamycin tartrate, chloramphenicol, thiamphenicol, minocycline hydrochloride, lincomycin hydrochloride, clindamycin hydrochloride, streptomycin sulfate, kanamycin sulfate, fradiomycin sulfate, gentamycin sulfate, spectinomycin hydrochloride, neomycin, vanomycin, tetracycline, ciprofloxacin, sulfanilic acidcycloserine, sulfisomidine, isoniazid, ethambutol, acyclovir, gancyclovir, vidabarine, azidothymidine, dideoxyinosine, dideoxycytosine, morphine hydrochloride, codeine phosphate, cocaine hydrochloride, pethidine, fentanyl citrate, polymeric forms of any of the above drugs and any combinations thereof.

Alternatively, the hydrophobic polymers may be useful in delivering hydrophobic drugs to another portion of the coated filament. Some non-limiting examples of hydrophobic drugs include non-steriodal anti-inflammatory agents, diflunisal, triclosan, salicylates, ziprasidone, raloxifene, paroxetine, glimepiride, anagrelide, modafinil, paroxetine, cabergoline, replaginide, glipizide, benzodiazepines, clofibrate, chlorpheniramine, dinitirate, digoxin, digitoxin, ergotamin tartate, estradiol, fenofibrate, griseofulvin, hydrochlorothiazide, hydrocortisone, isosorbide, medrogeston, oxyphenbutazone, prednisolone, prednisone, polythiazide, progensterone, spironolactone, tolbutamide, 10,11-dihydro-5H-dibenzo[a,d]cyclo-heptene-5-carboxamide, 5H-dibenzo[a,d]cycloheptene-5-carboxamide, taxoids, camptothecins, doxorubicin, michellamine B, vincristine, bryostatin-1, halomon, cisplatin, polymeric forms of any of the above drugs and any combinations thereof.

In embodiments, the drug or agent may be combined with a coupling agent to enhance the drugs ability to bond or interact with the hydrophobic or hydrophilic polymers described herein. The coupling agents act as an intermediary between the drug and the hydrophobic or hydrophilic polymers.

The coupling agent is typically a polyvalent organic compound and in particularly useful embodiments is a divalent compound. The coupling agent may be biologically inactive, or may itself possess biological activity. The coupling agent can also comprise other electrophilic or nucleophilic functional groups (including hydroxy groups, mercapto groups, amine groups, carboxylic acids, succinimidyl groups, as well as others) that can be used to modify the properties of the drug or polymers (e.g. for branching, for cross linking, etc.)

The coupling agent may incorporate other hydrolytically biodegradable groups such as alpha-ester (lactate, glycolate), e-caprolactone, ortho-ester, or enzymatically biodegradable groups such as amino acids. It may be a water-soluble, non-biodegradable segment such as a polyethylene glycol.

The coupling agent may be a water-insoluble, non-biodegradable segment such as polypropylene glycol, polyetherurethane, or poly(n-alkyl ether). It may be an amorphous or semicrystalline biodegradable polymer, such as poly(d,l-lactide), poly(trimethylene carbonate), poly(dioxanone), polyanhydride poly(orthoester) poly(glycolide), poly(l-lactide) poly(e-caprolactone) and copolymers of e-caprolactone, glycolide, trimethylene carbonate, dioxanone, d,l-lactide, l-lactide and d-lactide The coupling agent may have surfactant properties, such as a Pluronic block copolymer with polyethylene glycol and polypropylene glycol blocks. It may have polar or charged moieties, including carboxylic acid groups from poly(acrylic acid) and poly(alginates), sulfonic acid groups from poly(2-acrylamido-2-methyl-propanesulfonic acid) (AMPS), hydroxy groups from poly(vinyl alcohol), polysaccharides and poly(alginates), and amino groups from poly(L-lysine), poly(2,2-dimethylaminoethyl methacrylate) and poly(amino acids).

The coupling agent may be a segment that undergoes thermoreversible gellation, such as Pluronic F127 and poly(N-isopropyl acrylamide). It may incorporate structurally-reinforcing segments, such as polyetherurethane, polyesterurethane, etc.

The coupling agent may be a polyvalent, branched or unbranched, saturated or unsaturated, hydrocarbon chain, having from 1 to 25 carbon atoms, wherein one or more (e.g. 1, 2, or 3) of the carbon atoms is optionally replaced by (—O—), (—S—) or (—NR—).

The coupling agent may be a peptide, enzyme, protein, nucleotide, amino acid, polyamino acid or polypeptide.

Figure 2:
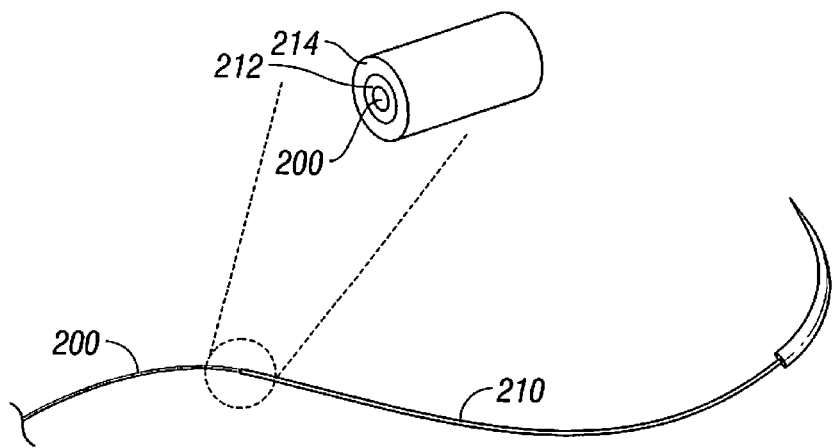
FIG. 2 shows a perspective view of a coated filament in accordance with a multi-layer embodiment described herein.

Turning now to FIG. 1, filament 100 is shown having coating 110 which includes a vinyl lactam polymer 112 and a lactone polymer 114. Coating 110 is shown as a phase separated coating wherein vinyl lactam polymer 112 and lactone polymer 114 are positioned on different portions of filament 100. It should, of course be understood that single phase coatings are embraced by this disclosure. In FIG. 2, a multiple layer coating 210 is shown on filament 200. Base coat 212 is applied to filament 200 prior to application of outer counting 214 which is made from a composition including a vinyl lactam polymer.

It is further envisioned that the filament coatings may further include a biocompatible copolymer having both hydrophilic and hydrophobic characteristics. The addition of the biocompatible copolymer having both hydrophilic and hydrophobic characteristics inhibits phase separation of the filament coating having a hydrophilic polymer and a hydrophobic polymer. The resulting filament coating is a single continuous phase rather than a phase separated partitioned coating. Some examples of useful biocompatible copolymers having both hydrophilic and hydrophobic characteristics include copolymers formed from polyalkylene oxides (such as polyoxyethylene and polyoxypropylene) copolymerized with lactone polymers. A particularly useful biocompatible copolymer having both hydrophilic and hydrophobic characteristics is a copolymer of Polytribolate® (Registered Trademark of Tyco Healthcare, Mansfield, Mass.), an absorbable polymer of ε-caprolactone, glycolide with poloxamer 188.

In embodiments, the filament coating may further include optional ingredients. Optional ingredients, as used herein, may represent up to about 10% by weight of the filament coating and include ingredients such as, emulsifiers, surfactants, dyes, fragrances and the like.

EXAMPLE 1

A coating solution containing 1% polyvinylpyrrilodone (PVP), 2% of a 10/90 glycolide/ε-caprolactone copolymer and 2% calcium stearoyl lactylate is prepared in methylene chloride. The coating solution is applied to the uncoated Polysorb® sutures using a Dietz and Schell coating apparatus with a line speed of 40 m/min and oven temperature of approximately 100° C. The coated sutures are dried at 40° C. overnight under vacuum. The dried solution forms a partitioned multiphase coating on the surface of the suture.

EXAMPLE 2

Polysorb® sutures are pre-coated with a composition containing 2% of a 10/90 glycolide/ε-caprolactone copolymer and 2% calcium stearoyl lactylate. A top coating containing 1% PVP in methylene chloride is applied to the pre-coated Polysorb® sutures using a Dietz and Schell coating apparatus with a line speed of 40 m/min and oven temperature of approximately 100° C. The coated sutures are dried at 40° C. overnight under vacuum. The dried solution forms a smooth, single phase coating on the surface of the suture.

EXAMPLE 3

A coating solution containing 1% polyvinylpyrrilodone (PVP), 2% of a 10/90 glycolide/ε-caprolactone copolymer, 2% calcium stearoyl lactylate and 0.5% Polytribolate® (a commercially available absorbable block copolymer of ε-caprolactone/glycolide/poloxamer 188) is formed. The coating solution is applied to the uncoated Polysorb® sutures using a Dietz and Schell coating apparatus with a line speed of 40 m/min and oven temperature of approximately 100° C. The coated sutures are dried at 40° C. overnight under vacuum. The dried solution forms a smooth, single phase coating on the surface of the suture.

It will be understood that various modifications may be made to the embodiments disclosed herein. Therefore, the above description should not be construed as limiting, but merely as an exemplification of preferred embodiments. Those skilled in the art will envision other modifications within the scope and spirit of this disclosure. Various modifications and variations of the coated filaments and uses thereof will be apparent to those skilled in the art from the foregoing detailed description. Such modifications and variations are intended to come within the scope of the following claims.

What is claimed is:

1. A medical device comprising at least one filament having a partitioned coating formed from a coating composition comprising a blend of a vinyl lactam polymer and a lactone polymer miscible in a common solvent wherein said partitioned coating is formed after driving off the common solvent.

2. The medical device of claim 1 wherein the vinyl lactam polymer comprises monomeric units selected from the group consisting of N-vinyl-pyrrolidone, N-vinyl-2-piperidone, and N-vinyl-caprolactam, N-vinyl methyl pyrrolidone, N-vinyl ethyl pyrrolidone, N-vinyl methyl caprolactam, and combinations thereof.

3. The medical device of claim 1 wherein the vinyl lactam polymer is polyvinyl pyrrolidone.

4. The medical device of claim 1 wherein the lactone polymer comprises polymers derived from monomeric units selected from the group consisting of lactide, glycolide, caprolactone, dioxanone, propiolactone, butyrolactone, valerolactone, decalactone, pivalolactone, stearolactone, palmitolactone, trimethylene carbonate and combinations thereof.

5. The medical device of claim 1 wherein the coating further comprises a metallic salt or fatty acid ester salt.

6. The medical device of claim 1 wherein the filament is a suture.

7. A medical device comprising a filament having a phase separated coating formed from a coating composition comprising a blend of a vinyl lactam polymer and a lactone polymer and a fatty acid ester salt wherein the polymers are miscible in a common solvent and said phase separated coating is formed after driving off the common solvent.

8. The medical device of claim 7 wherein the vinyl lactam polymer comprises monomeric units selected from the group consisting of N-vinyl-pyrrolidone, N-vinyl-2-piperidone, and N-vinyl-caprolactam, N-vinyl methyl pyrrolidone, N-vinyl ethyl pyrrolidone, N-vinyl methyl caprolactam, and combinations thereof.

9. The medical device claim 7 wherein the lactone polymer comprises monomeric units selected from the group consisting of lactide, glycolide, caprolactone, dioxanone, propiolactone, butyrolactone, valerolactone, decalactone, pivalolactone, stearolactone, palmitolactone and combinations thereof.

10. The medical device of claim 7 wherein the vinyl lactam polymer is polyvinyl pyrrolidone.

11. The medical device of claim 7 further comprising a hydrophilic drug.

12. The medical device of claim 7 further comprising a hydrophobic drug.

13. The medical device of claim 7 further comprising a hydrophilic and a hydrophobic drug.

14. A medical device comprising a filament having a phase separated coating formed from a coating composition comprising a drug, a coupling agent, and a blend of a vinyl lactam polymer and a lactone polymer wherein the polymers are miscible in a common solvent and said phase separated coating is formed after driving off the common solvent.

15. The medical device of claim 14 wherein the coupling agent is selected from the group consisting of peptides, enzymes, proteins, nucleotides, amino acids, polyamino acids, and polypeptides.

16. The medical device of claim 14 wherein the coupling agent comprises a polyvalent compound.

17. The medical device of claim 16 wherein the polyvalent compound comprises a branched hydrocarbon chain having 2 to 25 carbon atoms.

18. The medical device of claim 14 wherein the coupling agent is a thermoreversible material.

19. The medical device of claim 18 wherein the thermoreversible material comprises polyethylene oxide, polypropylene oxide, poly(N-isopropyl acrylamide) and combinations thereof.

20. The medical device of claim 14 wherein the drug comprises a hydrophobic drug.

21. A method of forming a partitioned coating on a filament comprising:
    forming a blend of a vinyl lactam polymer and a lactone polymer, wherein the polymers are miscible in a common solvent,
    applying the blend to the filament, and
    driving off the common solvent.

* * * * *